United States Patent [19]
Fischer

[11] 3,965,910
[45] June 29, 1976

[54] URINARY IRRIGATION VALVE

[75] Inventor: Michael Fischer, Winnetka, Ill.

[73] Assignee: Walpak Company, Wheeling, Ill.

[22] Filed: Apr. 28, 1975

[21] Appl. No.: 572,503

[52] U.S. Cl. .......................................... 128/349 R
[51] Int. Cl.[2] .................................... A61M 25/00
[58] Field of Search ............................ 128/349 R

[56] References Cited
UNITED STATES PATENTS

| | | | |
|---|---|---|---|
| 3,419,009 | 12/1968 | Ericson | 128/349 R |
| 3,513,849 | 5/1970 | Vaillancourt et al. | 128/349 R |

*Primary Examiner*—G.E. McNeil
*Attorney, Agent, or Firm*—Dressler, Goldsmith, Clement & Gordon, Ltd.

[57] ABSTRACT

A three-way urinary irrigation valve for use with a catheter is disclosed which is movable from a first position in which long term drainage takes place to a second position in which irrigating liquid can be introduced to a bladder, all while maintaining a closed system. The urinary irrigation valve includes a housing defining a first passage having an inlet leading to a bladder and an outlet leading to a drainage bag, and a second passage angularly disposed relative to the first passage and having an inlet at one end and an opposite closed end. A valve gate disposed in the second passage controls the flow of liquids between the inlet and outlet in the first passage, and between the inlet in the first passage and the second passage. An open-topped cap sealingly engages the housing adjacent the end of the second passage having the inlet. A resilient means normally biases the valve gate into a first position in which the valve gate cooperates with the cap to block flow through the second passage and permit flow between the inlet and outlet. To irrigate a bladder, an irrigating syringe can be inserted through the opening in the cap to act on the valve gate. The valve gate thereby assumes a second position in which flow to the outlet in the first passage is blocked, and a passage is defined between the second passage and the inlet of the first passage.

11 Claims, 4 Drawing Figures

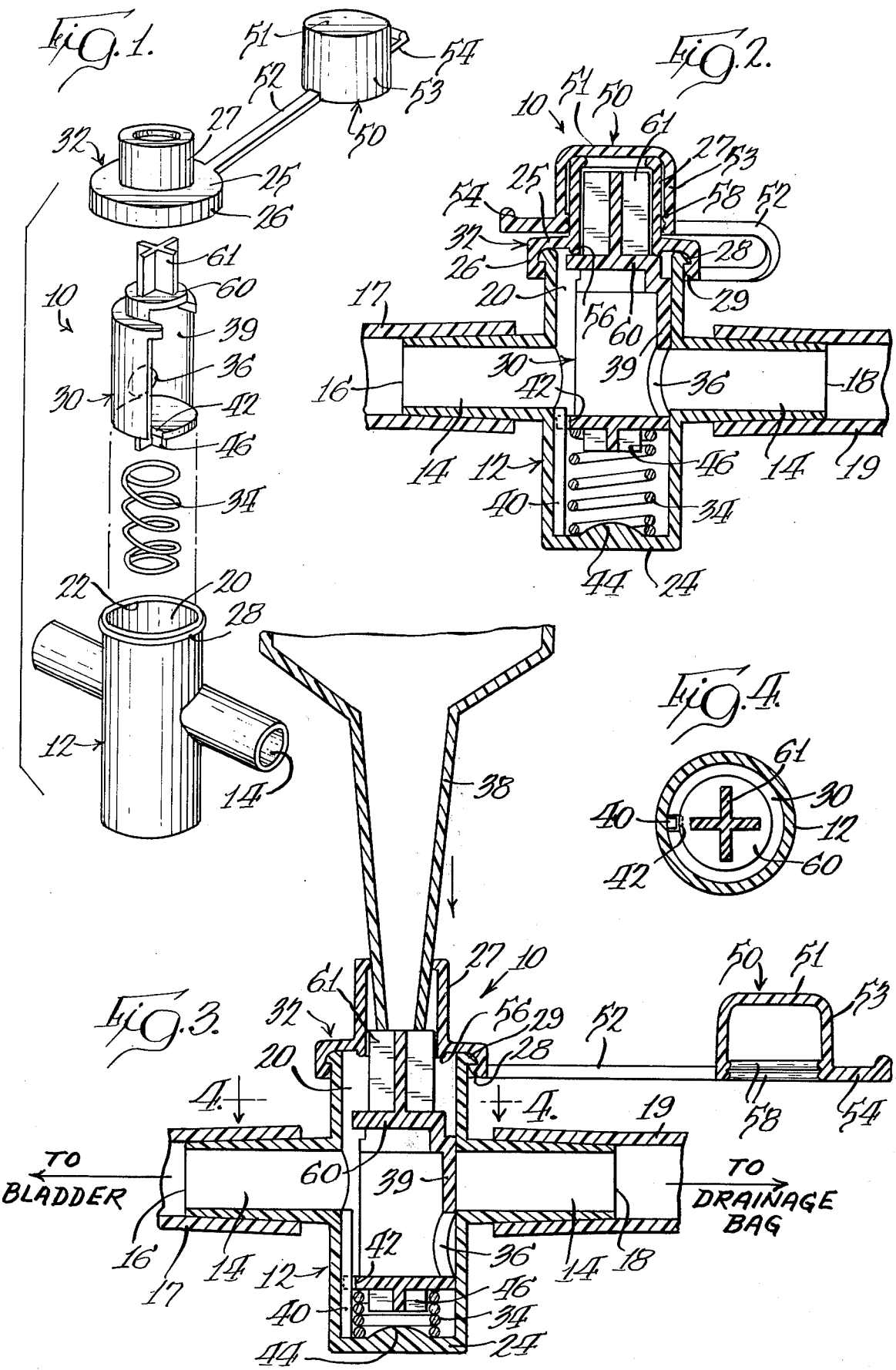

URINARY IRRIGATION VALVE

BACKGROUND OF THE INVENTION

This invention relates to three-way valves which maintain a completely closed system to perform regular irrigation and to collect urine specimens for urinalysis.

Two major varieties of catheters are available which are selected according to the use for which they are intended. Simple non-retention catheters are suitable for short term insertion in order to obtain specimens or to relieve acute bladder distention. Self-retaining catheters, to which the present invention relates, are designed to be left in place for long term drainage. The Foley balloon catheter is the most common form of self-retaining device. A modification of the Foley is the three-way catheter, which incorporates an additional lumen for the purpose of irrigating the bladder.

Infection stands as the most common and potentially dangerous result of urethral catherization. Many medical studies have demonstrated the prevalence of urinary tract infection in association with catheter drainage. A catheter cannot be passed with complete sterility because of the bacteria which normally resides within the distal urethra. It has been noted that two to three percent of patients will develop urinary tract infections after a single catherization. If the catheter remains indwelling, this figure rises rapidly with each passing day. Studies have shown that, after four to seven days, significant bacilluria may be found in 95% of patients with indwelling catheters.

Many attempts have been made to improve these statistics and great ingenuity has been expended in the design of catheters, drainage tubing, and collection bags in an effort to minimize the chances of infection. Measures such as careful techniques in catheter insertion, strict maintenance of a closed drainage system, and applications of topical antibiotic ointment to the urethral meatus have all been of some help in minimizing infection. Opinions vary on the use of prophylactic antibiotics such as sulfonamides or urinary anticeptic agents, such as nitrofurantoin, since no clinical study has conclusively demonstrated their advantage.

It is generally recognized that it is safest to utilize a completely closed system and to have the catheter, drainage tubing, and collection bag in continuity at all times. Unfortunately, it has been necessary to break or enter this closed system to perform regular irrigations and to collect urine specimens for urinalysis.

The single most effective method shown to minimize the infection problems in patients with indwelling catheters is the use of continuous bladder irrigation with a solution of antibiotics. Therefore, the use of a three-way self-retaining catheter is preferred. It has been shown that if a threeway irrigating system is introduced in a rigidly aseptic manner and the tubing is not disconnected to obtain a urine culture, urine can remain sterile at least up to ten days, and in some patients up to twenty days.

SUMMARY OF THE INVENTION

In accordance with the present invention, a three-way urinary irrigation valve is disclosed which permits long term drainage of a bladder and which permits solution from an irrigating syringe to flow into a bladder, while maintaining a closed system. The urinary irrigation valve comprises a generally cross-shaped housing defining a first passage extending therethrough having an inlet at one end and an outlet at an opposite end. A second passage is angularly disposed relative to the first passage and has an inlet at one end and an opposite end which is closed. An open-topped cap means sealingly engages the housing adjacent the inlet in the second passage.

A valve means such as a valve gate controls the flow between the inlet and outlet in the first passage and between the inlet of the first passage and the second passage. The valve gate defines a sealing means which cooperates with the cap means for blocking flow through the second passage when the valve gate is in a first position. The valve gate is movable to a second position wherein flow to the outlet in the first passage is blocked and wherein the valve gate defines a passage means permitting flow from the second passage to the inlet in the first passage when the valve gate is in a second position. The valve gate also defines a passageway therethrough whereby the inlet and outlet in the first passage are in communication when the valve gate is in the first position.

A resilient means is disposed in the housing and normally biases the valve gate into the first position, whereby an irrigating syringe can be employed to act on the valve gate to block off the flow between the inlet and outlet in the first passage and introduce an irrigating solution into the second passage, through the valve gate, and into the inlet in the first passage.

The resilient means may be disposed in the second passage abutting the closed end thereof. The valve gate has a first end abutting the resilient means and an opposite end having a longitudinally extending baffle means disposed inwardly of the portion of the housing which defines the second passage. Thus, the irrigating syringe acts on the baffle means to depress the valve gate and solution from the irrigating syringe can flow along the baffle means to enter the second passage.

The housing preferably defines cylindrically-shaped first and second passages. The opposite end of the valve gate is provided with a cylindrical segment which is centered thereon and from which the baffle means projects outwardly. The cylindrical segment is disposed inwardly of the portion of the housing defining the second passage and has a transverse dimension greater than the transverse dimension of the baffle means. When the valve gate is in the first position, the cap sealingly engages the cylindrical segment to form a seal between the atmosphere and the second passage.

BRIEF DESCRIPTION OF THE DRAWINGS

FIG. 1 is an exploded perspective view illustrating the urinary irrigation valve of the present invention;

FIG. 2 is an enlarged view in cross section of the urinary irrigation valve in a first position;

FIG. 3 is an enlarged cross-sectional view illustrating the urinary irrigation valve acted upon by an irrigation syringe and in a second position; and FIG. 4 is a sectional view taken along plane 4—4 of FIG. 3.

DETAILED DESCRIPTION OF THE PREFERRED EMBODIMENTS

Referring to the FIGURES, a three-way urinary irrigation valve 10 is disclosed which is adapted for use with a self-retaining catheter which is designed to be left in place for long term drainage from a bladder to a drainage bag when the valve is in a first position, but which can be acted upon by an irrigating syringe to block off passage to the drainage bag and permit irrigating liquid to be introduced through the valve to a bladder when the valve is in a second position.

Urinary irrigation valve 10 comprises a generally cross-shaped housing 12 which has walls defining first and second passages 14 and 20 which are angularly disposed relative to one another. First passage 14 extends through housing 12 and has an inlet 16 at one end and an outlet 18 at the opposite end of passage 14. Second passage 20 is angularly disposed relative to first passage 14, intersects first passage 14, and has an inlet 22 at one end of the passage and an opposite closed end 24. While a cross-shaped housing 10 is disclosed, other shapes are also suitable, such as an inverted T-shaped housing. Passages 14 and 20 are preferably cylindrically-shaped in cross-section, although other shapes may also be suitable.

The end of first passage 14 having inlet 16 is suitably connected to a catheter 17 (FIG. 2) which leads to a bladder, while the opposite end of first passage 14 having outlet 18 is sealingly engaged by a tube 19 which leads to a drainage bag.

A valve gate 30 disposed in second passage 20 controls the flow of liquids between the inlet 16 and outlet 18 and between inlet 16 and second passage 20. An open-topped cap means such as cap 32 is sealingly engaged to housing 12 adjacent the end of second passage 20 having inlet 22. As shown in FIGS. 1 and 2, cap 32 includes a generally cylindrical hollow wall 25, an outer sidewall 26 generally perpendicular to wall 25 and extending in one direction from the outer edge of wall 25, and an inner sidewall 27 generally perpendicular to wall 25 and extending in the opposite direction from the inner edge of hollow wall 25. Housing 12 has an outwardly projecting annular lip 28 at the end of passage 20 having inlet 22, and the outer sidewall 25 of cap 32 has an inwardly projecting annular lip 29 which engages lip 28 to facilitate in retaining cap 32 on housing 12.

Urinary irrigation valve 10 further includes a resilient means such as spring 34 which normally biases valve gate 30 into a first position illustrated in FIG. 2. Valve gate 30 defines a sealing means and cooperates with cap 32 for blocking flow through second passage 20 when the valve gate 30 is in the first position. In this position, a seal is formed between valve gate 30 and cap 32, thereby separating the atmosphere from second passage 20.

Valve gate 30 has a passage 36 extending therethrough. Passage 36 is aligned with first passage 14 when valve gate 30 is in the first position so that the inlet 16 and outlet 18 are in communication and normal drainage can take place between the bladder and drainage bag.

Valve gate 30 is movable from the first position illustrated in FIG. 2 to a second position illustrated in FIG. 3. An irrigating syringe 38 can be employed to depress valve gate 30 against the bias of spring 34 to move the valve gate from the normally biased first position to the second position.

In the second position, cap 32 is no longer sealingly engaged to valve gate 30 and valve gate 30 has sidewall portion 39 blocking flow to the outlet end 18 of first passage 14. Second passage 20 communicates with inlet 16, thereby enabling irrigating fluid to by introduced past valve gate 30 to inlet 16 which leads to the bladder. When the irrigating syringe 38 is withdrawn from urinary irrigation valve 10, spring 34 returns valve gate 30 to the first position. Thus, the closed system between the bladder and drainage bag remains closed even when irrigation is performed, thereby minimizing the possibility of infecting the urinary tract. According to the present invention, bacteria are prevented from entering the system because the integrity of the system is retained when an irrigating fluid is supplied to the bladder from an irrigating syringe.

Referring now to FIGS. 2-4, housing 12 preferably had a longitudinally extending key 40 projecting into second passage 20. Valve gate 30 includes a corresponding slot 42 in which key 40 is receivable. Key 40 and slot 42 guide the movement of valve gate 30 between the first and second positions and maintain the orientation of valve gate 30 with respect to housing 12 during movement of the valve gate.

To facilitate in maintaining the position of spring 34, the opposite end 24 of second passage 20 has a centrally positioned projection 44 limiting transverse movement of the spring. Additionally, the end of valve gate 30 abutting spring 34 may also have a centrally positioned projection 46 to center spring 34 and prevent transverse movement of the spring.

As shown in FIGS. 1-3, open-topped cap 32 is provided with a cover 50 which is connected to the cap by an elongated connector means 52. The cover 50 has a top wall 51 and a sidewall 53 which sealingly engages the cap 32 to further close off second passage 20 when the valve gate 30 is in the first position. Thus, the cover 50 further guards against leakage from second passage 20 and maintains the area between valve gate 30 and the opening in cap 32 sterile in order to prevent contamination and possible infection. Connector means 52 connects cover 50 and cap 32 and prevents the cover from being separated from the cap. The cap 32, cover 50 and connector means 52 and preferably unitary. Cap 32 and cover 50 have open ends facing in the same direction when the cover is not in sealing engagement with the cap. Therefore, connector means 52 is twisted to position cover 50 in sealing engagement with cap 32. The twist in connector means 52 provides a spring action which facilitates removal of the cover from the cap. Cover 50 is also provided with a handle means 54 protruding therefrom to facilitate in gripping the cover for removal from cap 32 when it is desired to irrigate.

To increase the sealing effect between cap 32 and valve gate 30, cap 32 is provided with an annular lip 56 projecting from the inner edge of wall 25 in the opposite direction as inner sidewall 27 and which engages the valve gate when the valve gate is in the first position. Similarly, cover 50 is provided with at least one annular lip 58 projecting inwardly from the sidewall 53 of cover 50 to further increase the sealing effect between cover 50 and cap 32.

The end of valve gate 30 which faces away from spring 34 has a solid cylindrical segment 60 centrally disposed in second passage 20 and having a diameter less than the inside diameter of second passage 20, and greater than the inside diameter of cap 32 as illustrated in FIGS. 1 and 2. When valve gate 30 is in the first position, lip 56 on cap 32 sealingly engages a marginal portion of cylindrical segment 60 to form a seal between the atmosphere and the second passage 20. A longitudinally extending baffle means 61, which may comprise plus-shaped intersecting walls, extends from cylindrical segment 60 and projects outwardly from valve gate 30. Baffle means 61 is adapted to extend between the inner sidewall 27 of cap 32 when valve gate 30 is in the first position, and be acted upon by irrigating syringe 38 to move valve gate 30 to the second position, as shown in FIG. 3. Consequently, the baffle means has a transverse dimension which is less than the inside diameter of the portion of housing 12 which defines second passage 20 and which is less than the inside diameter of cap 32.

When valve gate 30 is depressed and assumes the second position, liquid from irrigating syringe 38 can flow along the baffle means, enter second passage 20, and flow through the space between cylindrical segment 60 and the portion of housing 12 defining second passage 20 to continue through second passage 20 to inlet 16 and to the bladder (FIG. 3).

Suitable materials for the components of the three-way valve 10 include acrylonitrile-butadiene-styrene (ABS) for housing 12; polypropylene for valve gate 30; polyvinyl chloride (PVC) for cap 32, cover 50 and connector means 52; and any suitable metal for spring 34. Cap 32 is preferably formed from a material which will distort to accommodate a relatively wide range of sizes of irrigating syringes.

While this invention is susceptible of embodiment in many different forms, there is shown in the drawings and described herein in detail one specific embodiment, with the understanding that the present disclosure is to be considered as an exemplification of the principles of the invention and is not intended to limit the invention to the embodiment illustrated.

What is claimed is:

1. A urinary irrigation valve adapted to permit long term drainage and to permit solution from an irrigating syringe to flow into a bladder comprising a generally cross-shaped housing defining a first passage extending therethrough having an inlet and outlet, a second passage angularly disposed relative to said first passage, open-topped cap means on said housing adapted to cooperate in closing off said first passage, valve means controlling flow between said inlet and outlet and between said inlet and second passage, said valve means defining sealing means cooperating with said cap means for blocking flow through said second passage means when the valve means is in a first position and passage means permitting flow from said second passage through said inlet when the valve means is in a second position, said valve means also defining a passageway therethrough whereby said inlet and outlet are in communication when the valve is in said first position, and resilient means in said housing normally biasing said valve into said first position, whereby an irrigating syringe can be employed to act on said valve means to block off the flow between the inlet and outlet of said valve and introduce an irrigating solution through said valve means into said inlet.

2. A urinary irrigation valve as defined in claim 1 wherein said passages are generally cylindrical, said housing has a longitudinally extending key projecting into said first passage, and said valve means has a slot therein whereby said key and slot maintain the orientation of said valve means with respect to said housing when said valve means moves between said first position and said second position.

3. A urinary irrigation valve as defined in claim 1 wherein a cover sealingly engages said cap to further close off said second passage.

4. A urinary irrigation valve as defined in claim 3 wherein an elongated connector means connects said cap and said cover to prevent said cover from being separated from said cap, said cap and said cover having open ends facing in the same direction when said cover is not in sealing engagement with said cap, whereby said connector means is twisted to position said cover in sealing engagement with said cap and said twisted connector means provides a spring action to facilitate removal of said cover from said cap.

5. A urinary irrigation valve as defined in claim 1 wherein said cap includes a generally cylindrical hollow wall having an outer edge and an inner edge, an outer sidewall generally perpendicular to said hollow wall and extending in one direction from the outer edge of said hollow wall, and an inner sidewall generally perpendicular to said hollow wall and extending in the opposite direction from the inner edge of said hollow wall, said outer sidewall being provided with an inwardly projecting annular lip to increase the sealing effect between said cap and said valve means.

6. A urinary irrigation valve as defined in claim 3 wherein said cover includes a top wall and a sidewall and is provided with at least one annular lip projecting inwardly from said sidewall to further increase the sealing effect between said cover and said cap.

7. A urinary irrigation valve as defined in claim 1 wherein said passages are generally cylindrical, said valve means has a first end abutting said resilient means and an opposite end, said opposite end having a longitudinally extending baffle means disposed inwardly of the portion of said housing defining said second passage, whereby said irrigating syringe acts on said baffle means to depress said valve means and said solution from said irrigating syringe flows along said baffle means to enter said second passage.

8. A urinary irrigation valve as defined in claim 7 wherein said opposite end of said valve means has a cylindrical segment centered thereon from which said baffle means extends, said segment being disposed inwardly of the portion of said housing defining said second passage and having a transverse dimension greater than the transverse dimension of said baffle means, and said cap sealingly engaging said cylindrical segment when said valve means is in said first position.

9. A urinary irrigation valve as defined in claim 1 wherein said housing is formed of acrylonitrile-butadiene-styrene.

10. A urinary irrigation valve as defined in claim 1 wherein said cap is formed of polyvinyl chloride.

11. A urinary irrigation valve as defined in claim 1 wherein said valve means is formed of polypropylene.

* * * * *